United States Patent
Drews et al.

(10) Patent No.: US 10,675,149 B2
(45) Date of Patent: *Jun. 9, 2020

(54) HEART VALVE ASSEMBLIES

(71) Applicant: Medtronic, Inc., Minneapolis, MN (US)

(72) Inventors: Michael J. Drews, Palo Alto, CA (US); Donnell W. Gurskis, Belmont, CA (US); Stephen R. Bacich, Half Moon Bay, CA (US)

(73) Assignee: Medtronic, Inc., Minneapolis, MN (US)

(*) Notice: Subject to any disclaimer, the term of this patent is extended or adjusted under 35 U.S.C. 154(b) by 26 days.

This patent is subject to a terminal disclaimer.

(21) Appl. No.: 15/275,855

(22) Filed: Sep. 26, 2016

(65) Prior Publication Data
US 2017/0007398 A1    Jan. 12, 2017

Related U.S. Application Data

(63) Continuation of application No. 13/768,134, filed on Feb. 15, 2013, now Pat. No. 9,474,601, which is a (Continued)

(51) Int. Cl.
*A61F 2/24*      (2006.01)

(52) U.S. Cl.
CPC .......... *A61F 2/2409* (2013.01); *A61F 2/2412* (2013.01); *A61F 2250/006* (2013.01); (Continued)

(58) Field of Classification Search
CPC .... A61F 2/2427; A61F 2/2409; A61F 2/2418; A61F 2/2439; A61F 2/2463
See application file for complete search history.

(56) References Cited

U.S. PATENT DOCUMENTS 3,628,535 A   12/1971   Ostrowsky et al.
3,744,060 A    7/1973   Bellhouse
(Continued)

FOREIGN PATENT DOCUMENTS

DE      19532973      11/1996

OTHER PUBLICATIONS

International Preliminary Report on Patentability (PCT/US2005/002157) dated Jul. 27, 2006.

*Primary Examiner* — Brian E Pellegrino
(74) *Attorney, Agent, or Firm* — Dicke, Billig, & Czaja, PLLC

(57) ABSTRACT

A heart valve assembly includes a base including a multi-lobular annular shape within a plane, a valve member or other annular body including a multi-lobular shape complementary to the shape of the base, and cooperating connectors on the base and the annular body for connecting the annular body to the base. The base includes an anchoring ring, and a flexible cuff for attaching the base to a biological annulus. The base and the annular body include guides for aligning their multi-lobular shapes, e.g., visual, tactile, or other markers, or tethers that extend from the base that are slidable through the annular body. During use, the base is attached to a biological annulus, the annular body is directed adjacent the annulus, oriented such that the multi-lobular shape of the annular body valve member is aligned with the base, and the annular body is attached to the base.

12 Claims, 14 Drawing Sheets

Related U.S. Application Data continuation of application No. 12/574,611, filed on Oct. 6, 2009, now Pat. No. 8,377,119, which is a continuation of application No. 10/765,725, filed on Jan. 26, 2004, now Pat. No. 7,597,711.

(52) U.S. Cl.
CPC .............. *A61F 2250/0097* (2013.01); *A61F 2250/0098* (2013.01)

(56) References Cited

U.S. PATENT DOCUMENTS

| | | | |
|---|---|---|---|
| 4,259,753 A | 4/1981 | Liotta et al. | |
| 4,451,936 A | 6/1984 | Carpentier | |
| 4,705,516 A | 11/1987 | Barone et al. | |
| 4,851,000 A | 7/1989 | Gupta | |
| 4,892,541 A | 1/1990 | Alonso | |
| 4,976,689 A | 12/1990 | Buchbinder et al. | |
| 5,032,128 A | 7/1991 | Alonso | |
| 5,037,434 A | 8/1991 | Lane | |
| 5,061,278 A | 10/1991 | Bicer | |
| 5,071,431 A | 12/1991 | Sauter et al. | |
| 5,147,391 A | 9/1992 | Lane | |
| 5,469,868 A | 11/1995 | Reger | |
| 5,662,704 A | 9/1997 | Gross | |
| 5,716,370 A * | 2/1998 | Williamson, IV | A61F 2/2427 623/2.11 |
| 5,891,160 A | 4/1999 | Williamson, IV et al. | |
| 5,984,959 A | 11/1999 | Robertson et al. | |
| 6,066,160 A * | 5/2000 | Colvin | A61B 17/0487 606/151 |
| 6,217,611 B1 | 4/2001 | Klostemeyer | |
| 6,241,765 B1 | 6/2001 | Griffin et al. | |
| 6,254,636 B1 | 7/2001 | Peredo | |
| 6,371,983 B1 | 4/2002 | Lane | |
| 6,409,759 B1 | 6/2002 | Peredo | |
| 6,468,305 B1 | 10/2002 | Otte | |
| 6,716,244 B2 * | 4/2004 | Klaco | A61F 2/2409 623/2.4 |
| 6,776,785 B1 | 8/2004 | Yencho et al. | |
| 6,893,459 B1 | 5/2005 | Macoviak | |
| 7,597,711 B2 | 10/2009 | Drews et al. | |
| 8,021,421 B2 | 9/2011 | Fogarty et al. | |
| 8,377,119 B2 | 2/2013 | Drews | |
| 2003/0023302 A1 | 1/2003 | Moe et al. | |
| 2004/0015232 A1 | 1/2004 | Shu et al. | |
| 2004/0030381 A1 | 2/2004 | Shu | |
| 2005/0137686 A1 | 6/2005 | Salahieh et al. | |
| 2005/0137701 A1 * | 6/2005 | Salahieh | A61F 2/2418 623/2.38 |

\* cited by examiner

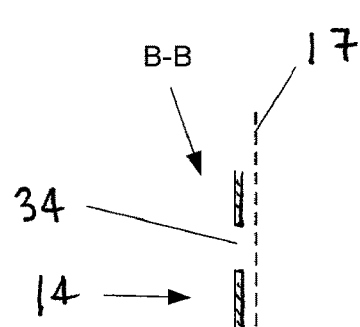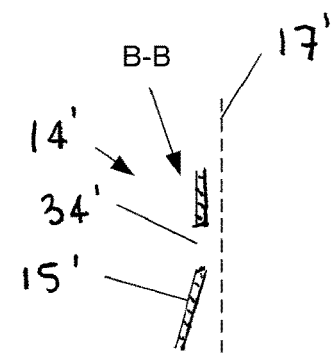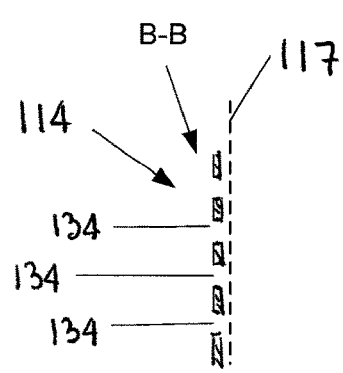
Fig. 12　　　Fig. 13　　　Fig. 14
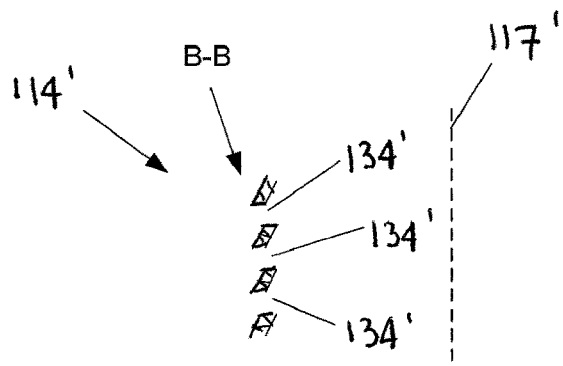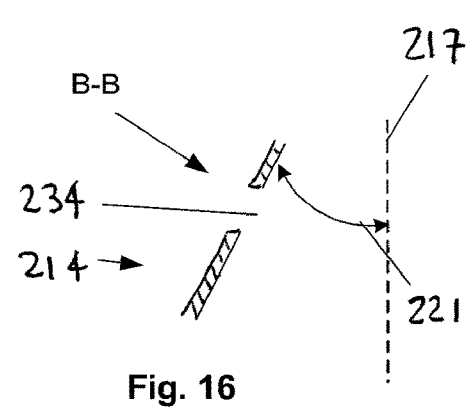
Fig 15　　　Fig. 16
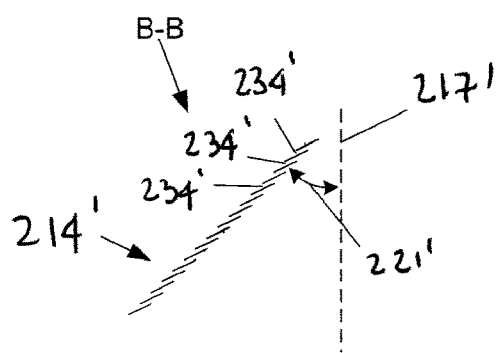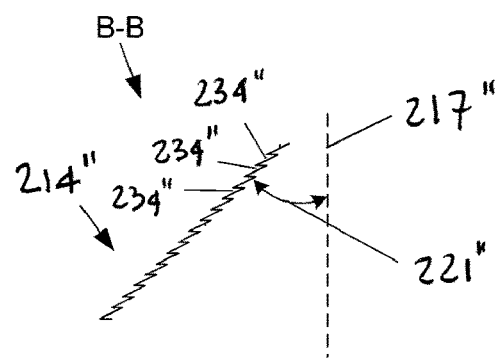
Fig. 17　　　Fig. 18

HEART VALVE ASSEMBLIES

RELATED APPLICATION DATA

This application is a continuation of U.S. patent application Ser. No. 13/768,134, filed Feb. 15, 2013, which is a continuation of U.S. patent application Ser. No. 12/574,611, filed Oct. 6, 2009, now issued as U.S. Pat. No. 8,377,119, which is a continuation of U.S. patent application Ser. No. 10/765,725, filed Jan. 26, 2004, now issued as U.S. Pat. No. 7,597,711, the disclosures of which are herein incorporated by reference in their entirety.

FIELD OF THE INVENTION

The present invention relates generally to heart valves that may be implanted into a patient, and, more particularly, to multiple component heart valve assemblies that may be assembled together, and to apparatus and methods for making and implanting them.

BACKGROUND

Prosthetic heart valves can replace defective human valves in patients. Prosthetic valves commonly include sewing rings, suture cuffs, or rings that are attached to and extend around the outer circumference of the prosthetic valve orifice. Because of their circular cross-sections, sewing rings that are implanted may not optimally fit the biological annulus into which a valve may be implanted. As a result, natural blood hemodynamics through and around the valve may be impaired, resulting in cloning, possible emboli production, and eventual calcification of the valve structure.

As patients grow, particularly pediatric patients, the leaflets of a valve may no longer be property sized to fit the annulus. Leaflets may also calcify or otherwise foul and need to be replaced. To replace the leaflets on a single-piece prosthetic valve, the entire valve must be removed, which may cause trauma to the annulus and jeopardize implantation of a replacement valve. Further, it may be difficult to work around and through leaflets of a valve to attach a leaflet-laden valve, possibly damaging the leaflets and extending the length of the valve replacement procedure.

Sewing rings can also be tedious and time consuming to secure to a valve orifice. To assemble multiple component heart valves, one component has to be sewn into another in vivo, resulting in a complex and time consuming process. The complexity of the procedure also provides a greater opportunity for mistakes and requires a patient to be on cardiopulmonary bypass for a lengthy period.

Multiple piece heart valves also typically require a significant amount of handling during implantation, potentially exposing the delicate leaflets to damage before or during in vivo implantation. Additionally, orientation of the components of a multiple piece heart valve is generally not defined by the device, making the implantation of the second piece of the valve less intuitive. The surgeon must align the components of the valve during in vivo assembly when limited access can impair dexterity and the fragile valve components are at risk of being damaged. Also, known multiple piece valves lack sufficient mechanical safeguards to insure that the surgeon will properly orient or secure the valve components. Once implanted, multiple component heart valves can have problems with the components fitting each other in a secure and stable manner. Improper fit can cause mechanical stress and hemodynamic anomalies leading to clotting, dislodgement or valve failure.

Accordingly, heart valves, particularly multiple piece valves that may be reliably implanted into biological heart annuluses, e.g., to maximize hemodynamic flow and/or ease implantation, would be useful.

SUMMARY OF THE INVENTION

The pretest invention is directed to heart valves that may be implanted into a patient, and, more particularly, to multiple component heart valve assemblies that may be assembled together, and to apparatus and methods for making and implanting them.

In accordance with one aspect of the present invention, a heart valve assembly is provided that includes a base member including a multi-lobular annular shape within a plane, an annular body including a multi-lobular shape complementary to the multi-lobular shape of the base member, and cooperating connectors on the base member and the annular body for connecting the annular body to the base member. In one embodiment, the connectors may include mating detents on the base member and annular body, e.g., one or more protrusions and one or more apertures for receiving corresponding protrusions therein.

In an exemplary embodiment, the base member may include an anchoring ring or other rigid base including one or more connectors thereon, and a flexible cuff for attaching the base to a biological annulus. The flexible cuff may include a sewing ring extending radially from the base and/or fabric or other material attached to and/or covering at least a portion of the base. In one embodiment, the base may include one or more windows for accommodating a fastener, e.g., a clip or suture, for attaching the base to the annulus.

In addition or alternatively, the annular body may include a frame carrying one or more leaflets to provide a valve member. Alternatively, the annular body may be a connecting member for connecting a valve member to the base member.

In accordance with another aspect of the present invention, a heart valve assembly is provided that includes a base member generally defining a plane sod a longitudinal axis substantially orthogonal to the plane, the base member including a multi-lobular annular shape within the plane, an annular body including a multi-lobular shape complementary so the multi-lobular shape of the base member, and guides on at least one of the base member and the annular body for aligning the multi-lobular shapes with one another about the longitudinal axis.

Optionally, cooperating correctors may be provided on the base member and the annular body for attaching the annular body to the base member. For example, the connectors may include mating detents on the base member and the annular body, e.g., one or more protrusions and one or more apertures for receiving corresponding protrusions therein.

In one embodiment, the guides may include visual markers on at (east one of the base member and the annular body that may aligned within one another when the multi-lobular shape of the annular body is aligned with the multi-lobular shape of the base member. In addition or alternatively, the guides may include tactile or audio markers that provide an indication to a user that the annular body is aligned with the base member. In another embodiment, the guides may include one or more tethers extending from the base member through the annular body such that the annular body is slidable along the tethers to align the annular body with the base member as the annular body is directed towards the base member. Optionally, the tethers may include ratchet elements spaced apart along a portion of the tethers, thereby provided a tactile indication as the annular body is directed towards the base member, e.g., to identify a distance from the annular body to the base member. Preferably, each tether extends through a port or other guide channel in the annular body, and the ratchet elements may engage the guide channel to allow the annular body to be directed towards the base element but preventing the annular body from being directed away from the base member.

In accordance with yet another aspect of the present invention, a method is provided for assembling a heart valve including a base member including a multi-lobular annular shape and a second device including a multi-lobular shape complementary to the multi-lobular shape of the base member. The second device may be moved adjacent 10 the base member, wherein the multi-lobular shape of the second device aligns with the multi-lobular shape of the base member, and the second device may then be attached to the base member. For example, the second device may be slid along one or more guide members towards the base member. In addition or alternatively, guides on the annular body and/or base member may include visual, auditory, and/or tactile markers that may be monitored to ensure that the annular body is aligned with the base member.

Once the second device contacts or is otherwise adjacent the base member, cooperating connectors on the second device and the base member may engage to secure the second device to the base member. In one embodiment, the second device may be a valve member, e.g., a single-piece heart valve. Alternatively, the second device may be a frame or other annular body to which a valve may be attached either before or after attaching the frame to the base member. In this alternative, guides may be provided to align and facilitate successive attachment of each component to one another.

In accordance with still another aspect of the present invention, a method is provided for implanting a heart valve within a biological annulus within a heart of a patient. Initially, a base member may be attached to the biological annulus, the base member having a multi-lobular annular shape corresponding generally to a cross-section of the annulus. A valve member including a multi-lobular shape complementary to the base member may be directed adjacent the annulus. The valve member may be oriented such that the multi-lobular shape of the valve member is aligned with the multi-lobular shape of the base member, and the valve member may be attached to the base member.

Other objects end features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 12-18 are cross-sectional views of various embodiments of the crown of FIG. 1, taken a bog section B-B, showing connectors thereon.

DETAILED DESCRIPTION OF THE PREFERRED EMBODIMENTS

1. Multiple-Component Heart Valve Assemblies

Figure 1:
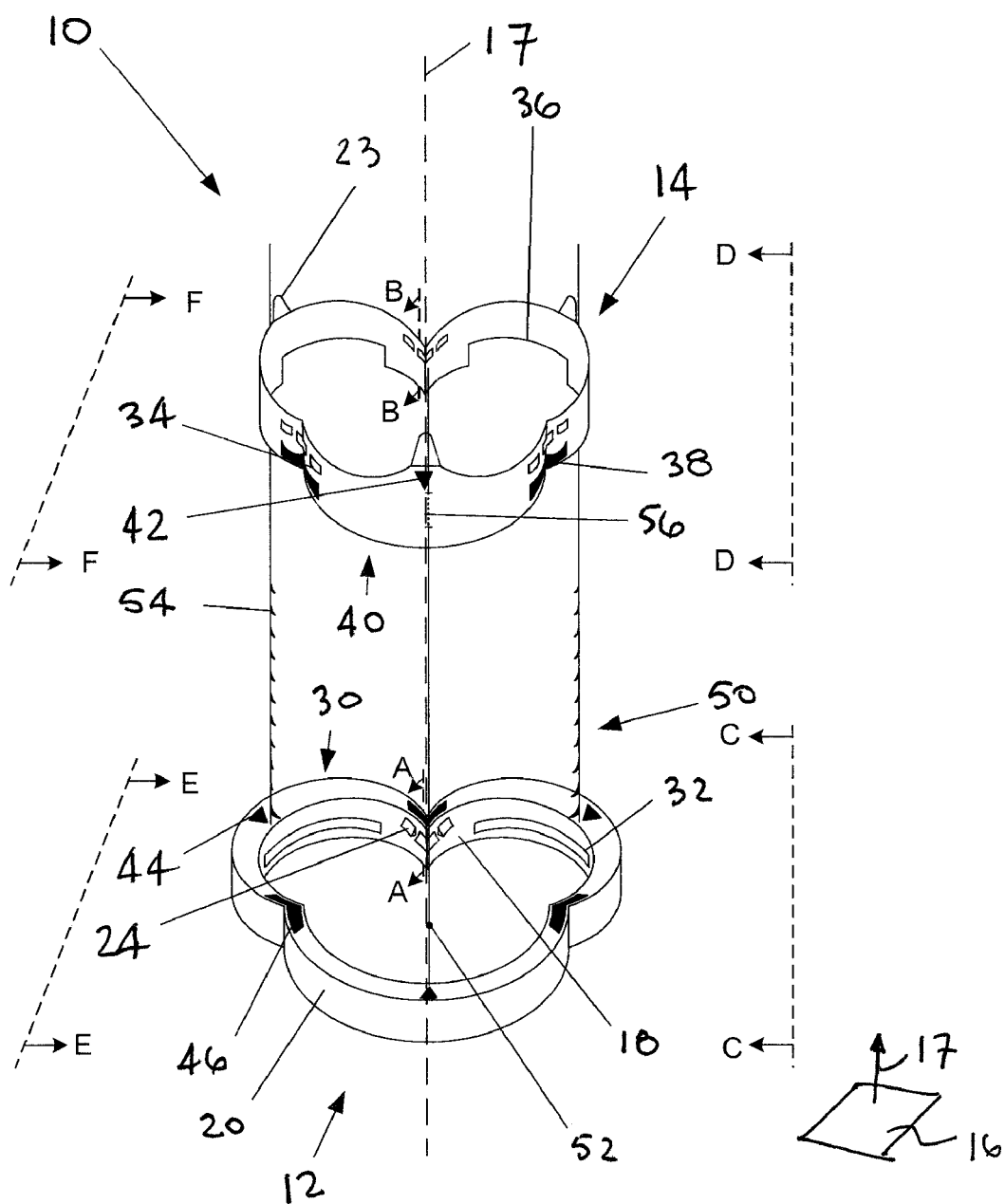
FIG. 1 is an exploded perspective view of an embodiment of a heart valve assembly, including a base and a crown.

Turning to the drawings, FIG. 1 illustrates a heart valve assembly 10 that generally includes a base member 12 and a valve member or "crown" 14. As described further below, the base member 12 and/or crown 14 may include one or more connectors for attaching the crown 14 to the base 12 and/or one or more guides for facilitating aligning and/or connecting the crown 14 with the base 12.

The base member 12 may be a generally annular shaped body lying in a plane 16, thereby defining a longitudinal axis 17 substantially orthogonal to the plane 16. The base member 12 may have a noncircular shape within the plane, such as a multi-lobular shape. Preferably, the base member 12 has a tri-lobular shape, i.e., including three lobes 30 separated by three cusps 28, corresponding generally to a cross-section of a biological annulus within which the base member 12 may be implanted, as explained further below. It will be appreciated that the base member 12 may define other noncircular shapes with in the plane 16, e.g., that may correspond to anatomy of a patient within which the heart valve assembly 10 may be implanted.

The base member 12 may include a substantially rigid anchoring ring or base 18 and a flexible cuff or sewing ring 20 that may extend around a periphery of the anchoring ring 18. The cuff 20 may simply be a layer of fabric or other material covering at least a portion of the anchoring ring 18. Alternatively, the cuff 20 may include a section of material (not shown) extending radially from the anchoring ring 18. The anchoring ring 18 and cuff 20 may be integrally formed as a single element or may be separate components attached to one another. In addition, the cuff 20 may be slidably or fixedly attached to the anchoring ring 18.

The crown 14 may be a generally annular shaped body having a noncircular, e.g., multi-lobular shape, complementary to the base member 12. Preferably, the crown 14 has a tri-lobular shape, similar to the base member 12, including three lobes 40 separated by cusps 38. In a preferred embodiment, the crown 14 is a valve member including on annular frame 22, and a plurality of leaflets (not shown for clarity) extending from the frame 22, e.g., attached to commissures 23. The frame 22 may include a plurality of struts (also not shown for clarity) that may be attached to and/or interact with the leaflets, similar to the struts disclosed in U.S. Pat. No. 6,371,983, the entire disclosure of which is expressly incorporated by reference herein. Alternatively, the crown 14 may be a connecting device, such as the connection adapter elements shown in U.S. patent application Ser. No. 10/646,639, filed 22 Aug. 2003, the entire disclosure of which it expressly incorporated by reference herein.

Components of the heart valve assembly 10, e.g., the base 18 and/or sewing ring 20 of the base member 12 and/or crown 14, may be made from one or more materials, such as one or more alloys, such as alloys of stainless steel, nickel titanium ("Nutinol"), cobalt-chrome (e.g., ELGILOY® from Elgin Specialty Metals, Elgin, Ill.; CONICHROME® from Carpenter Metals Corp., Wyomissing, Pa.), molybdenum (e.g., molybdenum TZM alloy, as disclosed, for example, in International Pub. No. WO 03/082363 A2, published 9 Oct. 2003, which is herein incorporated by reference in its entirety), and/or tungsten-rhenium (e.g., as disclosed in International Pub. No. WO 03/082363). In addition or alternatively, the components may be made from polymers, such as polyester (e.g., DACRON® from E. I. Du Pont de Nemours and Company, Wilmington, Del.), polypropylene, polytetrafluoroethylene (PTFE), expanded PTFE (cPTFE), polyether ether ketone (PEEK), nylon, polyetherblock co-polyamide polymers (e.g., PEBAX® from ATO-FINA, Paris, France), aliphatic polyether polyurethanes (e.g., TECOFLEX® from Thermedics Polymer Products, Wilmimgton, Mass.), polyvinyl chloride (PVC), polyurethane, thermoplastic, fluorinated ethylene propylene (PEP). In addition or alternatively, the components may be from or include other materials, such as extruded collagen, silicone, echogenic, radioactive, radiopaque material or combinations thereof. Exemplary radiopaque materials that may be used include barium sulfate, titanium, stainless steel, nickel-titanium alloys, tantalum, and/or gold.

Any or all elements of the heart valve assembly 10, for example, the cuff 20, may include a matrix for cell ingrowth, a fabric, or other flexible material, e.g., a covering (not shown) that may act as a matrix for cell ingrowth, and/or that may be penetrated with a fastener used to attach the cuff 20 to an annulus within which the heart valve assembly 10 is implanted. Exemplary fabric material may include polyester (e.g., DACRON® from E. I. du Pont de Nemours and Company, Wilmington, Del.), polypropylene, PTFE, ePTFE, nylon, extruded collagen, silicone, and/or combinations thereof. Optionally, the cuff 20 may be an o-ring, or may include a cushioned material, double velour material, and the like, attached using glue or other adhesives and/or fasteners.

Optionally, the heart valve assembly 10 and/or any fabric therein may also be filled and/or coated win one or mote agent delivery matrices known to those skilled in the art, a therapeutic agent, and/or a diagnostic agent. These agents may include radioactive materials; radiopaque materials, cytogenic agents; cytotoxic agents; cytostatic agents; thrombogenic agents, for example, polyurethane, cellulose acetate polymer mixed with bismuth trioxide, and ethylene vinyl alcohol; lubricious, hydrophilic materials; phosphor cholene; anti-inflammatory agents, for example, non-steroidal anti-inflammatories (NSAIDs), such as cyclooxy-genase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa., indomethacin; mefenamic acid), COX-2 inhibitors (e.g., VTOXX® from Merck & Co., Inc., Whitehouse Station, N.J.; CELEBREX® from Pharmacia Corp, Peapack, N.J.; COX-1 inhibitors); immunosuppressive agents, for example, Sirolimus (RAPAMUNE®, from Wyeth, Collegeville, Pa.) or matrix metalloproteinase (MMP) inhibitors (e.g., tetracycline and tetracycline derivatives) that act early within the pathways of an inflammatory response. Examples of other agents that may be used are disclosed in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11) (1641-1649. The entire disclosures of these references and any others cited therein are expressly incorporated by reference herein.

The base member 12 and the crown 14 may include cooperating detents or other connectors for attaching the crown 14 to the base member 12. Turning to FIGS. 2-9, the base member 12 may include protrusions 24, e.g., tabs or prongs, extending from at least one of the anchoring ring 18 and the cuff 20. The protrusions 24 may be separate from or integral with the cuff 20 and/or anchoring ring 18. In an exemplary embodiment, shown in FIG. 2, the protrusions 24 extend from the anchoring ring 18 such that they define a sloping proximal surface 24a to accommodate sliding along the crown 14 (not shown) and a blunt distal surface 24b for interlocking with the crown 14 to prevent separation of the crown 14 from the base member 12. The protrusions 24 may be resilient, e.g., may be based to extend in a desired direction, e.g., substantially parallel or transverse to the longitudinal axis 17, yet may be resiliently compressed or deflected to facilitate connection of the crown 14 to the base member 12.

Figure 20:
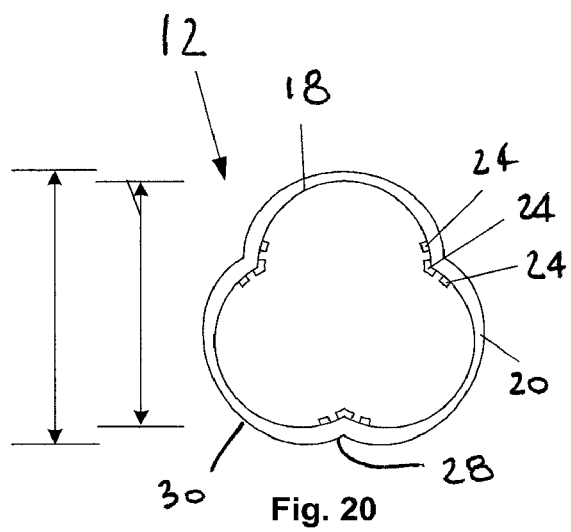
FIG. 20 is a cross-sectional view of the base of FIG. 1, taken along section E-E.
Figure 21:
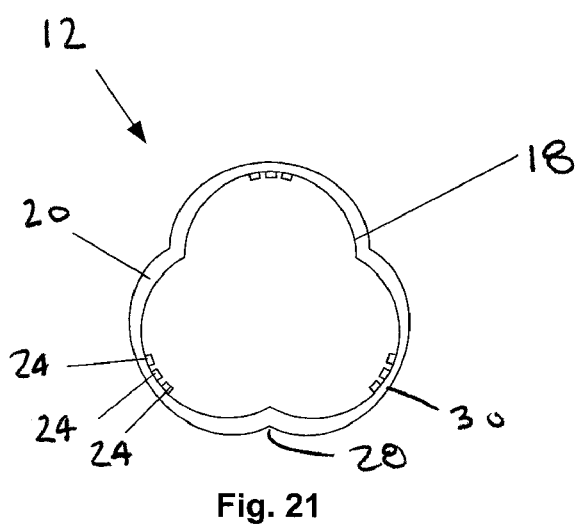
FIG. 21 is a cross-sectional view of an alternative embodiment of a base that may be incorporated into a heart valve assembly.

For example, as shown in FIGS. 1 and 20, a plurality of protrusions 24 may be provided on the anchoring ring 18, e.g., spaced apart from one another about a periphery of the base member 12. In a preferred embodiment, the base member 12 has three sets of protrusions 24, e.g., one set disposed in each lobe 26, offset from one another approximately 120° about the longitudinal axis 17. As shown in FIG. 20, the protrusions 24 may be located along an inner surface at the cusps 28 of the base member 12, although alternatively, the protrusions may be provided at the outer apices and/or along inner edges of the lobes 30, such as along the outer edges of the lobes 30, as shown in FIG. 21.

Figure 3:
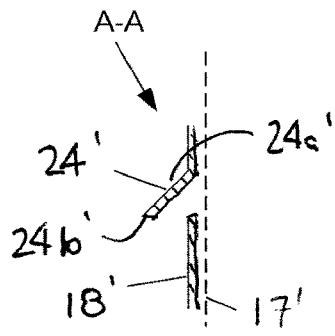

FIG. 3 shows an alternative embodiment of a protrusion 24,' namely a flange extending from the anchoring ring 18'. The protrusion 24' may be biased such that a free end 24b' of the flanges extends diagonally away from the anchoring ring 18', thereby defining a sloped proximal surface 24a.' The protrusion 24' may be caused to deflect against or into the wall of the anchoring ring 18' but may resiliently return outwardly once released, e.g., such that the free end 24b' is received in an aperture of a crown 14' (not shown, see. e.g., FIG. 13) to secure the crown 14' to the anchoring ring 18.'

Figure 2:
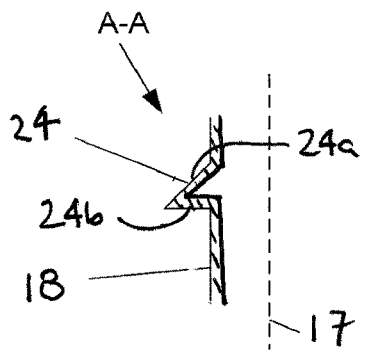
FIGS. 2-9 are cross-sectional views of various embodiments of the base of FIG. 1, taken along section A-A, showing connectors thereon.
Figure 4:
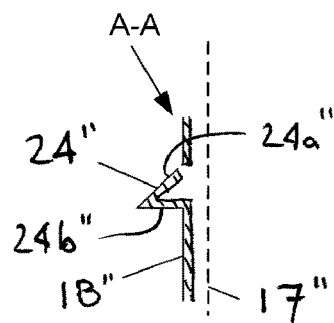
Figure 5:
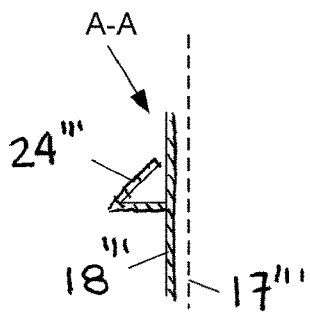
Figure 6:
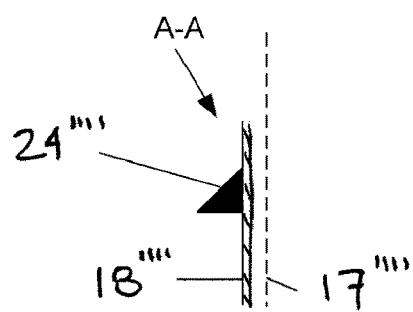

FIG. 4 illustrates another alternative embodiment of a protrusion 24″ that includes a brunt distal surface 24b″ and a proximal free end 24a″ that may be biased outwardly yet collapsible, similar to the embodiment of FIG. 2. FIG. 5 illustrates still another embodiment of a protrusion 24‴ with a free end unattached to an anchoring ring 18.‴ In addition or alternatively, as shown in FIG. 6, a protrusion 24″″ may be provided that is solid, and may be filled with a material, such as the radiopaque or other materials described above orator an agent delivery matrix, therapeutic agent, and/or diagnostic agent, also as described above.

Figure 7:
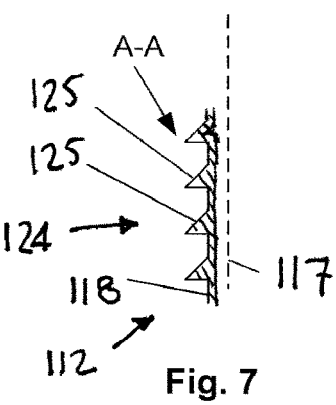

Turning to FIG. 7, another embodiment of a connector 124 is shown that may be provided on an anchoring ring 118 (or other component of a base member 112). The connector 124 includes a plurality of detents 125 (e.g., four shown) spaced apart axially from one another along a direction of the longitudinal axis 117.

Figure 8:
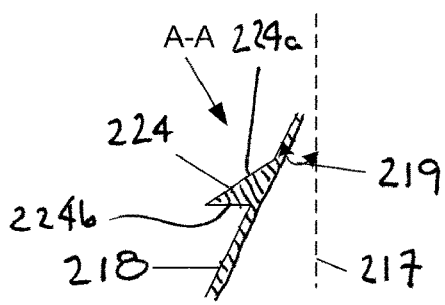

Turning to FIG. 8, another embodiment of an anchoring ring 218 is shown that has a shape that tapers axially relative to longitudinal axis 217. In the embodiment shown, the anchoring ring 218 includes an inner surface that defines an angle 219 with respect to the longitudinal ax is 217. A protrusion 224 extends from the inner surface of the anchoring ring 218 that includes a sloped proximal surface 224a and a blunt distal surface 224b, similar to previous embodiments. Alternatively, the protrusion 224 may extend from the outer surface or other location (not shown) of the anchoring ring 218.

Figure 9:
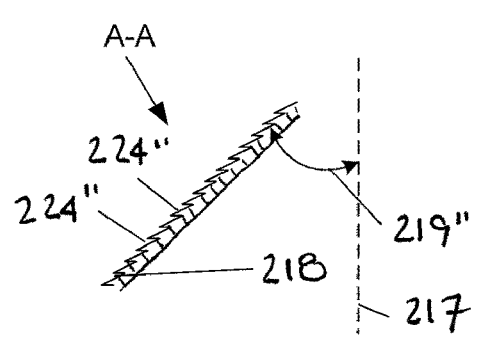

FIG. 9 illustrates another alternative embodiment of an anchoring ring 218″ that includes a plurality of protrusions 224″ (e.g., sixteen shown) that are spaced apart from one another along a direction defining an angle 219″ with the longitudinal axis 217″ to provide a ratcheting connector.

Figure 10:
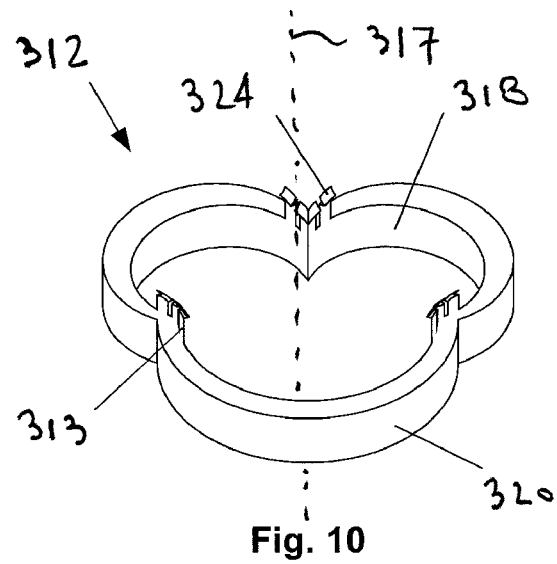
FIGS. 10 and 11 are perspective views of alternate embodiments of a base that may be incorporated into a heart valve assembly.

Turning to FIG. 10, another embodiment of a base member 312 is shown that includes a plurality of protrusions 234 on legs 313 extending from the base member 312 in a direction substantially parallel to a longitudinal axis 317. The legs 313 may be integrally formed with the base member 312 or may be attached to the base member 312, and may extend proximally or distally (not shown) from the base member 312.

Figure 11:
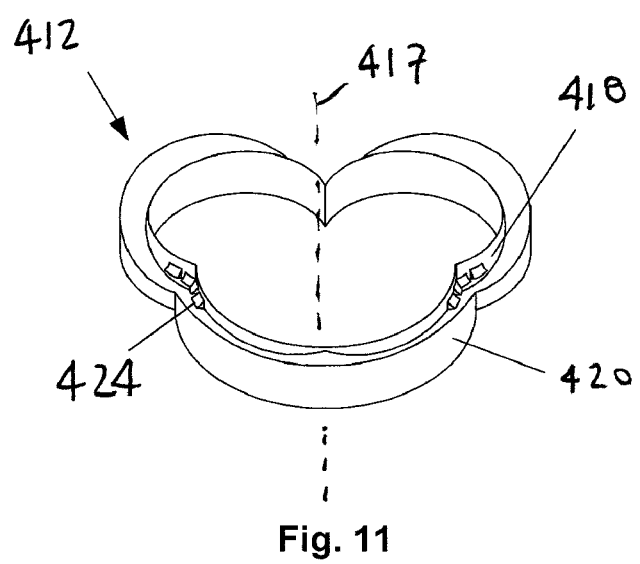

Turning to FIG. 11, another embodiment of a base member 412 is shown that includes connectors, i.e. tabs or protrusions 424e located on an outer surface of the base member 412, i.e., from the anchoring ring 418 or the cuff 420 thereof. Preferably, the cuff 420 is shaped and/or is attached to the anchoring ring 418 to ensure that the protrusions 424 are exposed to be engaged with mating connectors on a crown (not shown) attached to the base member 412.

Returning to FIG. 1, optionally, the anchoring ring 18 may include one or more base attachment windows 32, e.g., formed in the lobes 30. The windows 32 may extend radially through the anchoring rings 18 to accommodate fasteners (not shown) being inserted therethrough. For example, if cuff 20 covers the base attachment windows 32, a clip or suture (not shown) may be inserted into the window 32 from the inside, through the cuff 20 and into surrounding tissue to attach the base member 12 to the tissue, as explained more particularly below. Exemplary fasteners and methods for implanting heart valves or devices using fasteners are disclosed in U.S. application Ser. No. 10/681,700, filed Oct. 8, 2003, and entitled "Attachment Device and Methods of Using the Same." The entire disclosure of this reference and any references cited therein are expressly incorporated herein by reference.

Similarly, the crown 14 may include one or more crown attachment windows 36, which may be openings or recesses in the wall or frame of the crown 14, preferably extending completely through the wall of the crown 14. The crown attachment windows 36 may be provided in the lobes 40 such that they are aligned with the base attachment windows 32 in the base member 12 when the crown 14 is attached to the base member 12.

Turning to FIG. 12, the crown 14 may include one or more cooperating connectors that may interact with the connectors on the base member 12 to secure the crown 14 to the base member 12. For example, as shown, a plurality of apertures 34, e.g., holes, slots, pockets, cavities, and the like, may be provided in the crown 14 for receiving the protrusions 24 therein. The material adjacent the apertures 34 may be sufficiently flexible and/or resilient to yield and allow the protrusions 24 to be received therein. The apertures 34 may have a variety of shapes corresponding to the shapes of the protrusions 24, e.g., square, rectangular, circular, or oval shape.

Alternatively, protrusions (not shown) may be provided on the crown 14 instead of or in addition to the apertures 34, each including a sloping distal surface and a blunt proximal surface. The sloping edge of a protrusion on the crown 14 may slide along the sloping edge of a corresponding protrusion on the base member 12 until the blunt edges interlock to secure the crown 14 relative to the base member 12. Optionally, at least one of the base member 12 and the crown 14 may include a track or channel adjacent the protrusions for guiding the protrusions on the crown 14 into alignment with the protrusions on the base member 12.

Turning to FIGS. 13-18, alternative embodiments of crowns are shown that include apertures that may be used to received connectors from base members, such as those shown in FIGS. 3-9. Optionally, a covering (not shown) may be attached to or otherwise surround the crowns, as long as the apertures are exposed to receive the mating connectors from the base members.

FIG. 13 illustrates an embodiment of a crown 14' that includes a tapered section 15' angled relative to the longitudinal axis 17' and an aperture 34.' In this embodiment, the base member 12' (not shown) may include a complementary taper such that crown 14' may fit into or over, and, consequently, mate with the base member 12.'

Turning to FIG. 14, another embodiment of a crown 114 is shown that includes a connector including a plurality of apertures 134 (four shown) spaced apart axially from one another along a direction of a longitudinal axis 117. Apertures 134 may be provided at the distal and/or proximal (not shown) ends of the crown 114 such that the apertures 134 may receive corresponding protrusions 125 from the base member 112 (not shown, see FIG. 7).

FIG. 15 shows another alternative embodiment of a crown 114' that includes multiple apertures 134," each having an adjacent wall section that is angled relative to the longitudinal axis 217.' These angled or ramped wall sections may facilitate protrusions on a base member (not shown) being received therein when the crown 114' is being connected to the base member.

FIG. 16 shows yet another embodiment of a crown 214 having a tapered shape defining an angle 221 that is complementary to the base member 212 shown in FIG. 8. The crown 214 includes an aperture 234 in the inner surface, although the aperture 234 may be provided at other locations corresponding to the protrusion 224 on the base member 212.

Figure 19:
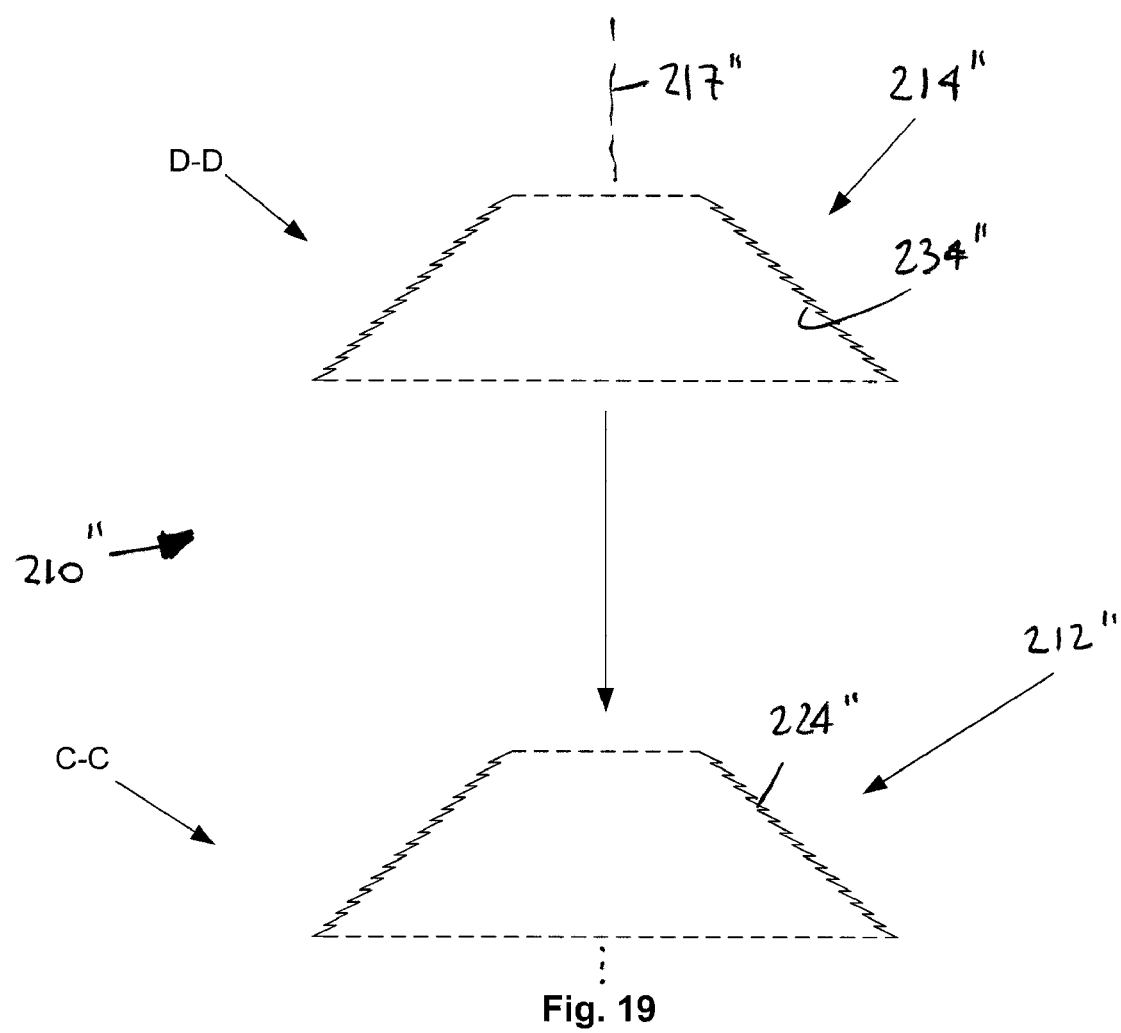
FIG. 19 is a cross-section of another embodiment of a heart valve, including a plurality of connectors on a base and crown that may ratchet together.

Turning to FIGS. 17-19, additional embodiments of crowns 214,' 214" are shown that have a tapered shape, and include a plurality of detents 234,' 234" (fifteen shown) for interlocking with cooperating detents 424" on base member 212" (shown in FIGS. 9 and 19). In the embodiment shown in FIG. 17, apertures 234' extend completely through a wall of the crown 214'. Alternatively, as shown in FIG. 18, the crown 214" may include apertures 234" that do not extend completely through a wall of the crown 214," thereby defining pockets.

As shown in FIG. 19, the crown 214" and the base member 212" include complementary tapered shapes, e.g., tapering from a larger distal dimension to a smaller proximal dimension. In this embodiment, the detents 234," are on the inner surface of the crown 214" and the detents 224" are on the outer surface of the base member 212." Thus, when the crown 214" is directed over the base member 212," at least a portion of the base member 212" is received in the crown 214" such that the detents 234," 224" ratchet together. The cooperating detents 224," 234" may interlock when the crown 214" is directed against the base member 212," thereby attaching the crown 214" to the base member 212."

Alternatively, the crown and base member may be tapered smaller from their proximal to distal ends (not shown). In this alternative, the detents may be provided on an outer surface of the crown and on an inner surface of the base member to allow the detents to ratchet together. It will be appreciated that the crown 214" and base member 212" shown in FIG. 19 are not to scale. Preferably, the slope of the taper is such that the length of the crown 214" and base member 212" is longer than the change in their cross-sections, thereby maximizing the opening through the crown 214" and base member 212," e.g., to maximize hemodynamic flow through the resulting heart valve assembly 210."

Figure 22:
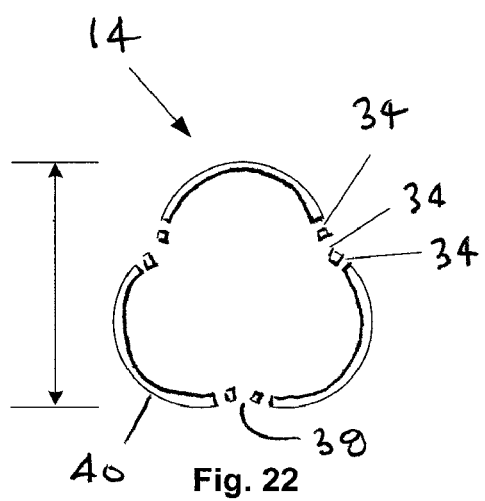
FIG. 22 is a cross-sectional view of the crown of FIG. 1, taken along section F-F.
Figure 23:
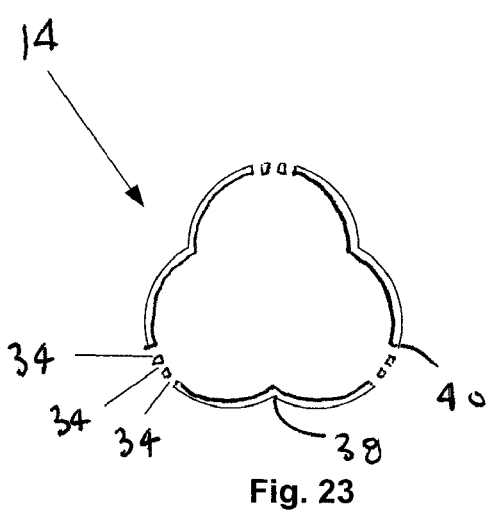
FIG. 23 is a cross-sectional view of an alternative embodiment of a crown that may be connected to the base shown in FIG. 21 to provide a heart valve assembly.

During assembly, when a crown, such as the crown 14 shown in FIGS. 1 and 22 is rotated about the longitudinal axis 17 relative to a base member 12, such as that shown in FIGS. 1 and 20, the lobes 40 of the crown 14 may be aligned with the lobes 30 of the base member 12. When the crown 14 is then placed against the base member 12, the protrusions 24 and apertures 34 may be aligned with one another such that the protrusions 24 may be received in corresponding apertures 34 to attach the crown 14 to the base member 12.

Although the exemplary embodiment shown in FIG. 1 shows protrusions 24 provided on the base member 12 and corresponding apertures 34 are provided on the crown 14, it will be appreciated that the protrusions and apertures may be interchanged on the base member 12 and crown 14 (not shown). As long as each protrusion on one of the base member and crown can be aligned with a corresponding aperture or protrusion on the other of the crown and the base member, cooperating connectors may be used to attach the crown to the base member.

Returning to FIG. 1, in addition or alternatively to the cooperating connectors described above, the base member 12 and/or crown 14 may include one or more guide markers for facilitating aligning the crown 14 with the base member 12. For example, the base member 12 and crown 14 may include a set of one or more guide markers 42, 44 that may be raised, textured, colored, radiopaque, and/or echogenic markers on a surface of the base member 122 and/or crown 14. The guide markers may provide a visual indication (e.g., directly and/or using an imaging apparatus), an auditory indication, and/or a tactile indication of the relative orientation and/or location of the crown 14 with the base member 12, e.g., about the longitudinal axis 17.

For example, as shown in FIG. 1, visual guide markers 42, 44 may be provided on the crown 14 and the base member 12, e.g., at one or more of the cusps 38, 28. As shown, the markers 42 are provided on an outer surface of the crown 14 and on a proximal surface of the base member 122. Alternatively or in addition, guide markers (not shown) may be provided on the lobes 40, 30, and/or on inner surfaces, proximal surfaces, and/or distal surfaces of the crown 14 and/or the base member 12. Thus, the visual markers 42 on the crown 14 may align with the markers 44 on the base member 12 when the crown 14 is aligned with the base member 12. A user observing the crown 14 being directed towards the base member 12, e.g., from above, may be informed that the crown 14 is properly oriented and/or may be properly connected to the base member 12 based upon Hoc visual markers 42, 44. Optionally, the visual markers 42, 44 may include symbols, e.g., triangles, circles, rectangles, and the like (not shown), that may be easily identified, e.g., to inform a surgeon of the location on the crown 14 and/or base member 12 associated with a particular symbol.

In addition or alternatively, tactile markers, such as tab markers 46 may be provided on the base member 12 and/or, optionally, on the crown 14. As shown in FIG. 1, the tab markers 46 are raised portions extending from the upper or proximal surface of the anchoring ring 18 at the cusps 28. To form the tab markers 46, a height of the anchoring ring 18 (parallel to the longitudinal axis 17) may be varied, e.g., making the height smaller at the lobes 30 and larger at the cusps 28 thin such that portions of the anchoring ring 18 at the cusps 28 extend proximally, thereby defining the tab markers 46. Stated differently, the proximal surface of the anchoring ring 18 may have a scalloped shape, e.g., where the height of the anchoring ring 18 peaks at the cusps 28 and defines valleys at the lobes 30.

In order to mate with the base member 12, the distal surface of the crown 14 may have a complementary shape. For example, the cusps 38 of the crown 14 may have a smaller height than the lobes 40 such that the tab markers 46 may be received in recesses (not shown) in the crown 14. Thus, when the crown 14 is oriented about the longitudinal axis 17 relative to the base member 12, the complementary shapes of the base member 12 and crown 14 may only permit the crown 14 to be mated with the base member 12 when the complementary shapes, e.g., the tab markers 46 and recesses, fit together. Thus, the user may receive a tactile indication when the crown 14 is be aligned with the base member 12 in order to ensure that the multi-lobular shapes of the crown 14 and base member 12 are aligned before connecting them together.

In addition or alternatively, the guides may include one or more elongate guide members 50, e.g., including depth markers 52 and/or unidirectional or bidirectional retention elements, e.g., ratcheting elements 54. As explained further elsewhere herein, these guide members may also provided connectors for attaching the crown 14 to the base member 12. The guide members 50 may be threads, filaments, wires, or other tethers that extend from the base member 12. The tethers 50 may be attached to, pre-threaded through, or otherwise placed on the base member 12, e.g., at spaced apart intervals, preferably at the ends of the lobes 30 such that tethers 50 may be aligned with the commissures 23 on the crows 14. For example, the tethers 50 may be attached to the base member 12 during manufacturing or before or during implantation of the heart valve assembly 10.

Figure 27:
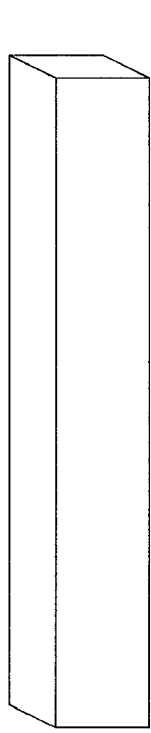
FIGS. 27-29 are perspective views of various embodiments of a guide member.
Figure 28:
Figure 29:
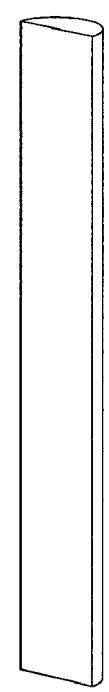

The tethers 50 may be formed from a variety of materials, similar to other components of the heart valve assembly 10, as described elsewhere herein, e.g., a fine gauge wire or suture material. The tethers 50 may be stiff or flexible, and/or may be resiliently bendable or plastically pliable. In addition, the tethers 50 may have a variety of cross-sections. For example, FIG. 27 shows a guide member 50' having a square or rectangular cross-sectional shape. FIG. 28 shows a guide member 50" having a circular or oval cross-sectional shape, and FIG. 29 shows a guide member 50''' having a semi-circular or semi-oval cross-sectional shape.

Optimally a guide tube (not shown) may be provided through which each tether 50 may be inserted. The guide tube may be a substantially rigid, semi-rigid, or flexible tubular body, e.g., a hypotube or polyamide tube. Such guide tubes may enhance the column strength of the tethers during their use to guide a crown towards a base member. The guide tubes may be slidable relative to the tethers such that guide tubes may be removed proximally from around the tethers during a procedure, as explained further below.

Figure 24:
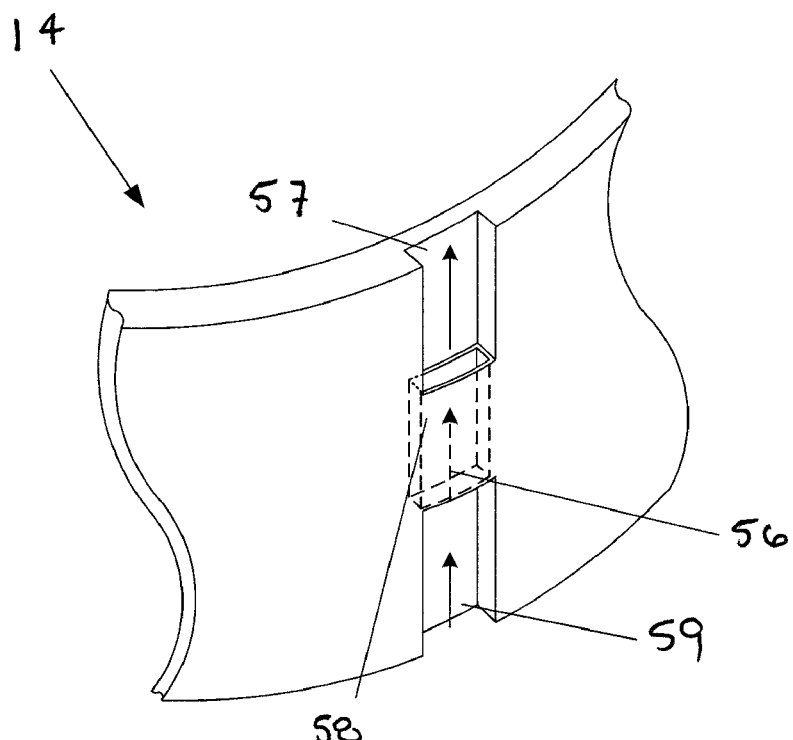
FIGS. 24-26 are details of various embodiments of a guide channel that may be provided on a crown.
Figure 25:
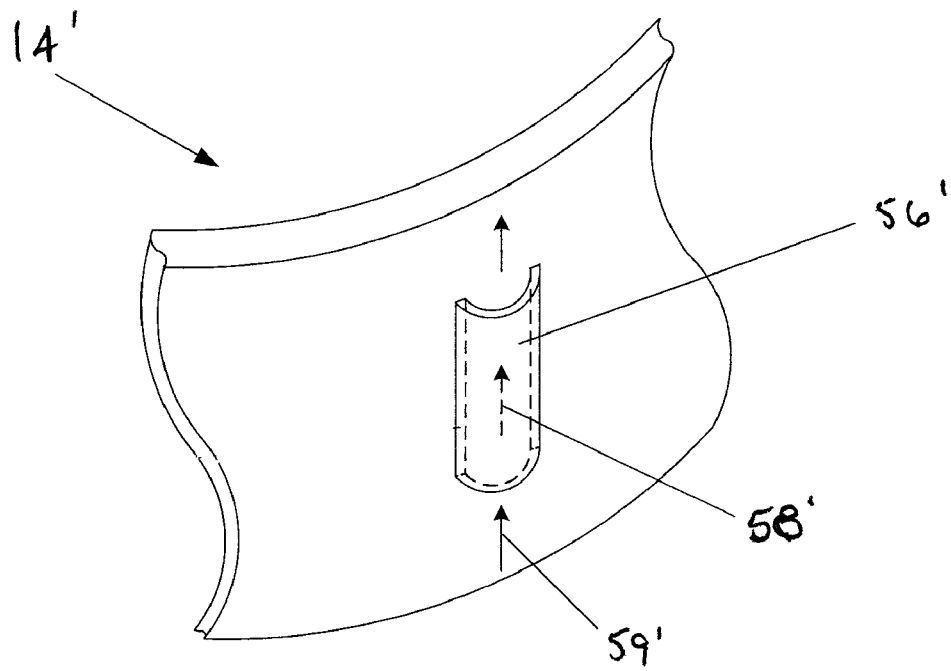
Figure 26:
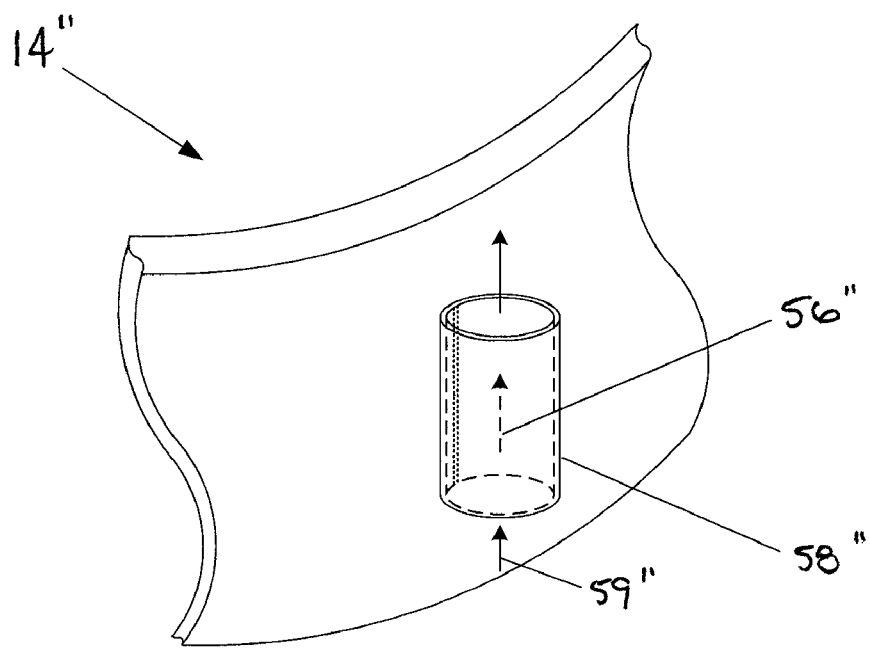

Turning to FIGS. 24-26, the crown 14 may include one or more ports or guide channels through which a guide member, such as the tethers 50 shown in FIG. 1, may be introduced. For example, as shown in FIG. 24, a guide channel 56 is shown that may be formed in a wall of the crown 14. In the embodiment shown, a recess 57 may be provided in the crown 14, e.g., in an outer surface (shown) or an inner surface (not shown) thereof, that extends axially along the crown 14. A cover 58 may extend across at least a portion of the recess 57, thereby defining the guide channel 56 thereunder. A guide member, such as tether 50 described above (not shown), may be inserted through the guide channel 56, e.g., in the direction shown by arrows 59. The guide channel 56 may have a variety of cross-sections, e.g., a rectangular cross-section, as shown, or shown, or alternatively, a square, semi-circular or other at least partial elliptical shape (not shown), depending upon the shape of the tether 50. If a guide tube is provided around the tether, the guide channel 56 may have a size large enough to slidably receive the guide tube therethrough.

Turning to FIG. 25, an alternative embodiment of a guide channel 56' is shown that may be formed by and/or in a wall of the crown 14.' For example, transverse slots 57' may be created in the wall of the crown 14' at two locations axially disposed from one another, thereby creating a guide channel 56' under the wall 58' through the openings 57.' Alternatively, a separate piece of material may be attached to the wall of the crown 14' to create the guide enamel 56.'

Turning to FIG. 26, yet another embodiment of a guide channel 56" is shown extending from a crown 14." In this embodiment, the guide channel 56" may be a tubular section of material 58" attached to the wall of the crown 14,' e.g., by an adhesive, sutures, and the like. The guide channel 56" may have a cylindrical shape, as shown, or other shapes (not shown). Optionally, the guide channels may include a guide tube therein, e.g., similar to the guide tubes described above for reinforcing the tethers 50.

Returning to FIG. 1, when tethers 50 (or other guide members, not shown) are inserted through guide channels (not shown) at corresponding locations in the crown 14, the crown 14 may be slidable along the tethers 50. Thus, the crown 14 may be lowered towards the base member 12 along the tethers 50. Preferably, the tethers 50 and corresponding guide channels are attached at the ends of the lobes 30, 40 of the base member 12 and crown 14.

Once the crown 14 is towered to meet the base member 12, the tethers 50 may be tightened or deployed to attach the crown 14 to the base member 12. The tethers may be used m conjunction with other connectors described herein, e.g., to form a redundant connection, or may be used atone to form both the connection between the crown 14 and the base member 12, while also acting as a guide to orient the devices.

To facilitate guiding the crown 14, the tethers 50 may include ratcheting elements 54, e.g., pawls or other detents, that may interact with the crown 14 and/or the guide channels. The ratcheting elements 54 may provide a tactile indicator of the distance from the crown 14 to the base member 12 and/or may prevent the crown 14 from being removed once it is directed towards the base member 12. For example, the ratcheting elements 54 may include sloping proximal surfaces and blunt distal surfaces, allowing the crown 14 to be directed down the tethers 50, but preventing them from being directed back up. Alternatively, the ratcheting elements 54 may including sloping proximal and distal surfaces, allowing the crown 14 to be directed down or up the tethers 50, but provided a resistance to movement.

In addition, the ratcheting elements 54 may include one or more sets of detents spaced apart at different distances along the tethers 50. For example, a first set of detents (not shown) may be provided at a predetermined distance from the base member 12, e.g., several centimeters. When the crown 14 contacts the first set of detents, the user may hear or feel the detents, thereby providing a tactile or auditory indication of the distance from the crown 14 to the base member 12. A second set of detents (also not shown) may then be provided to indicate that the crown 14 has been towered into its final position seated against the base member 12. Optionally, additional intermediate sets of detents may be provided spaced apart between the first and second sets, thereby providing a depth gauge that may inform the user how far the crown 14 has been towered or has left to be lowered.

In addition or alternatively, the detents may vary in size along the length of the tethers. For example, larger detents may be provided at predetermined intervals (not shown), provided greater auditory and/or tactile feedback to the user. In alternative embodiments, the detents may decrease in size from the ends of the tethers 50 towards the base member 12, may increase in size towards the base member 12, or may vary in some other desired manner, depending upon the feedback intended to be provided to the user.

II. Methods for Making Heart Valve Assemblies

The components of the heart valve assemblies described herein may be manufactured using methods well known to those skilled as the art. For example, manufacturing techniques that may be used include molding, machining, casting, forming (e.g., pressure forming), crimping, stamping, melting, screwing, gluing, welding, die cutting, laser cutting, electrical discharge machining (EDM), etching or combinations thereof.

Heart valve assemblies disclosed in U.S. Pat. Nos. 6,241, 765, 6,371,983, and 5,976,183 may be modified such that they may incorporated into a crown or may be attached to a valve connector adaptor, such as those described herein. The entire disclosures of these references and any others cited therein are expressly incorporated herein by reference. Other heart valves that may be incorporated into a heart valve assembly, as described herein, may include, for example, the Advantage Bileaflet heart valve, Parallel valve, Freestyle stentless aortic valve, Hancock Porcine heart valve, Hancock apical left ventricular connector model 174A, Hancock valved conduit models 100, 105, 150, Hall Medtronic heart valve, Hall Medtronic valved conduit, MOSAIC® heart valve, Intact porcine tissue valve (by Medtronic, Inc. Minneapolis, Minn.), Angelini Lamina-flo valve (by Cardio Carbon Company, Ltd., England), Bjork-Shiley single-disk, monostrut and caged-disk valves (Shiley, Inc., now-defunct, previously of Calif.), Wada-Cutter valve and Chitra Cooley-Cutter valve (by Cutter Biomedical Corp., San Diego, Calif.), Angioflex trileaflet polyurethane valve (by Abiomed, Inc., Danvers, Mass.), ATS AP Series heart valve and ATS Standard heart valve (by ATS Medical, Inc., Minneapolis, Minn.), ANNULOFLFLO® annuloplasty ring, ANNU-FLEX® annuloplasty ring, CARBSEAL® valved conduit, ORBIS® Universal aortic and mitral valve, pediatric/small adult valve, R series valve, SUMIT® mitral valve, TOP HAT® aortic valve, OPTTFORM® mitral valve, MITRO-FLOW SYNERGY® PC stented aortic pericardial bioprosthesis, the SYNERGY® ST stented aortic and mitral porcine bioprosthesis (by CarboMedics, Inc., Austin, Tex., ON-X® prosthetic heart valve (by MCRI®, LLC, Austin, Tex.), Starr-Edwards SILASTIC® ball valve, Starr-Edwards 1000, Starr-Edwards 1200, Starr-Edwards 1260, Starr-Edwards 2400, Starr-Edwards 6300, Starr-Edwards 6500, Starr-Edwards 6520, Carpentier-Edwards porcine tissue valve, Carpentier-Edwards pericardial prosthesis, Carpentier-Edwards supra-annular valve, Carpentier-Edwards annuloplasty rings, Duromedics valve and PERIMOUNT® heart valve (by Edwards Lifesciences Corp., Irvine, Calif.); Cross-Jones Lenticular disc valve (by Pemco, Inc.), Tissuemed stented porcine valve (by Tissuemed, Ltd., Leeds, England), Tekna valve (by Baxter Healthcare, Corp., Deerfield, Ill.), Komp-01 mitral retainer ring (by Jyros Medical Ltd., London, England), SJM® Masters Series mechanical heart valve, SJM® Masters Series aortic valved graft prosthesis, ST. JUDE MEDICAL® mechanical heart valves, ST. JUDE MEDICAL® mechanical heart valve Hemodynamic Plus (HP) series, SJM REGENT® valve, TORONTO SPV® (Stentless Porcine Valve) valve, SIM BIOCOR® valve, SJM EPIC® valve (St. Jude Medical, Inc., St. Paul, Minn.), and Sorin Bicarbon, Sorin Carbocast, Sorin Carboscal Conduit, Sorin Pericarbon and Sorin Pericarbon Stentless (by Snim S.p.A., Italy).

Any elements, sub-assemblies, or the entire heart valve assemblies described herein may be coated, e.g., by dip-coating or spray-coating methods known to one having ordinary skill in the art, utilizing materials such as PTFE (e.g., TEFLON® from E. I. du Pont de Nemours and Company, Wilmington, Del.), polyester (e.g., DACRON® from E. I. du Pont de Nemours end Company, Wilmington, Del.), gelatin, gel, other polymers or combinations thereof. One example of a method used to coat a medical device for vascular use is provided in U.S. Pat. No. 6,358,556 by Ding et al. The entire disclosure of this reference is incorporated herein by reference. Time release coating methods known to one having ordinary skill in the art may also be used to delay the release of an agent in the coating. The coatings may be thrombogenic or anti-thrombogenic.

The heart valve assemblies or any elements thereof (e.g., the base member) may be covered with a fabric, for example, polyester (e.g., DACRON® from E. I. du Pont de Nemours and Company, Wilmington, Del.), polypropylene PTFE (e.g., TEFLON® from E. I. du Pont de Nemours and Company, Wilmington, Del.), ePTFE, nylon, extruded collagen, gel, gelatin, silicone, or combinations thereof. Methods of covering an implantable device with fabric are known to those having ordinary skill in the art, for example, sintering, spray coating, adhesion, loose covering, dipping, or combinations thereof.

III. Methods for Implanting Heart Valve Assemblies

Figure 30:
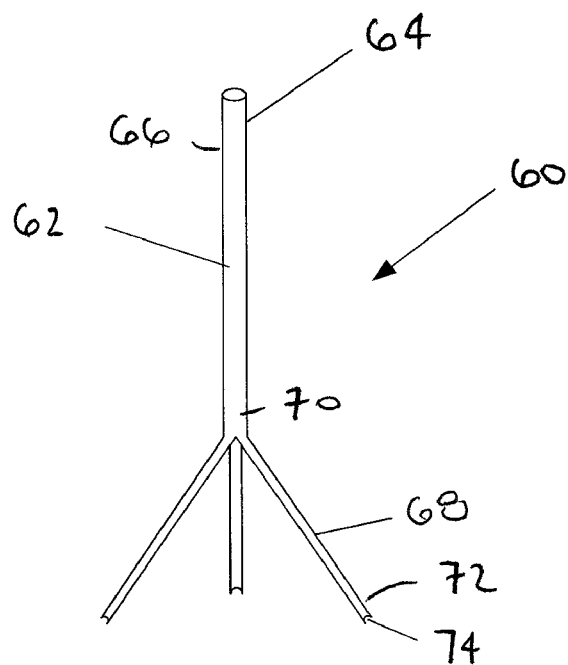
FIG. 30 illustrates an embodiment of a valve holder, including connectors for releasably carrying a component of a heart valve assembly during implantation.
Figure 33:
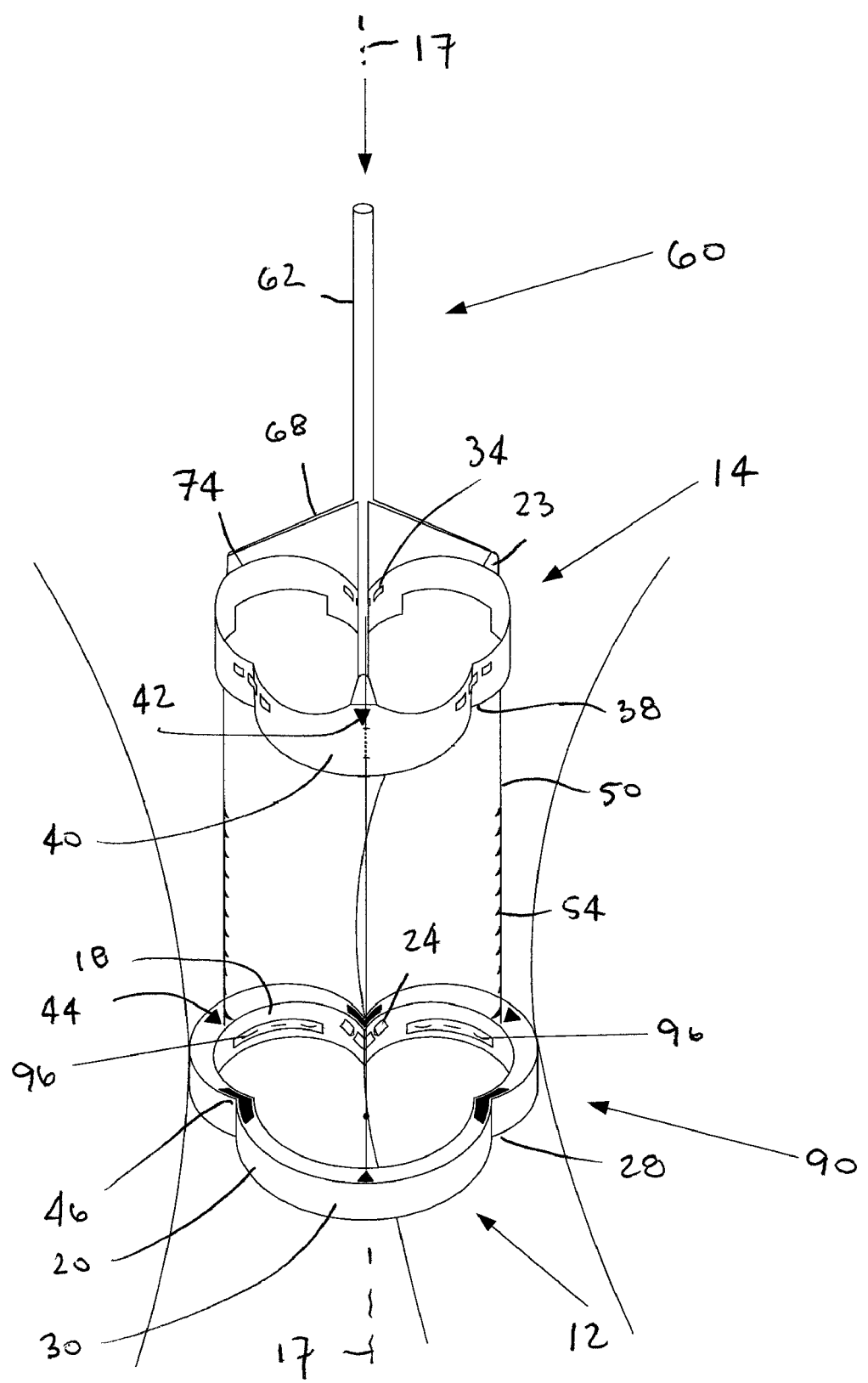

Turning to FIG. 30, an exemplary embodiment of a tool as shown, namely a valve driver or holder 60. Generally, the holder 60 may include an elongate shaft 62 including a handle 64 on a proximal end 66 and a plurality of arms 68 on a distal end 70 thereof. The shaft 62 may be a substantially rigid and/or malleable body that may be fixed or rotatable relative to the arms 68. Free ends 72 of the arms 68 may include connectors 74 that may be configured for releasably holding a base member and/or crown (not shown), such as those described above. Although three arms 68 are shown, it will be appreciated that more or fewer arms may be provided (not shown), if desired. The connectors 74 may be remotely triggered, e.g., from an actuator (not shown) on the handle 64, to attach and/or release a base and/or crown. FIG. 33 shows the holder 60 carrying a crown 12 using the connectors 74 on arms 68.

Turning to FIGS. 31-35, a method is shown for implanting a heart valve assembly within a biological annulus 90, which may be the site for replacement of an existing natural or previously implanted heart valve, such as a tricuspid, mitral, aortic, or pulmonary valve within a patient's heart (not shown). The annulus 90 may have multiple, for example two or three natural lobes 92 (three lobes being shown in FIG. 31 with one lobe cut-away). Although the method described below refers generally the heart valve assembly 10 shown in FIG. 1, it will be appreciated that any of the components described herein may be implanted using similar procedures.

Before implanting the heart valve assembly 10, the patient may be prepared for the procedure using known methods. For example, the patient may be placed on cardiopulmonary bypass (CPS), and the patient's heart may be exposed, e.g., by sternotomy, thoracotomy, or other open or minimally invasive procedure. An incision may be created in the blood vessel above the valve being replaced (not shown), e.g., the aorta for an aortic valve replacement, in order to access the annulus 90. The existing natural or prosthetic heart valve (also not shown) may be removed from the annulus 90 using known methods. A base member 12 may be selected based upon the anatomy encountered, e.g., having a plurality of lobes 30 matching the lobes 92 of the annulus 90 and/or having a cross-sectional dimension corresponding to the interior cross-section of the annulus 90.

Figure 31:
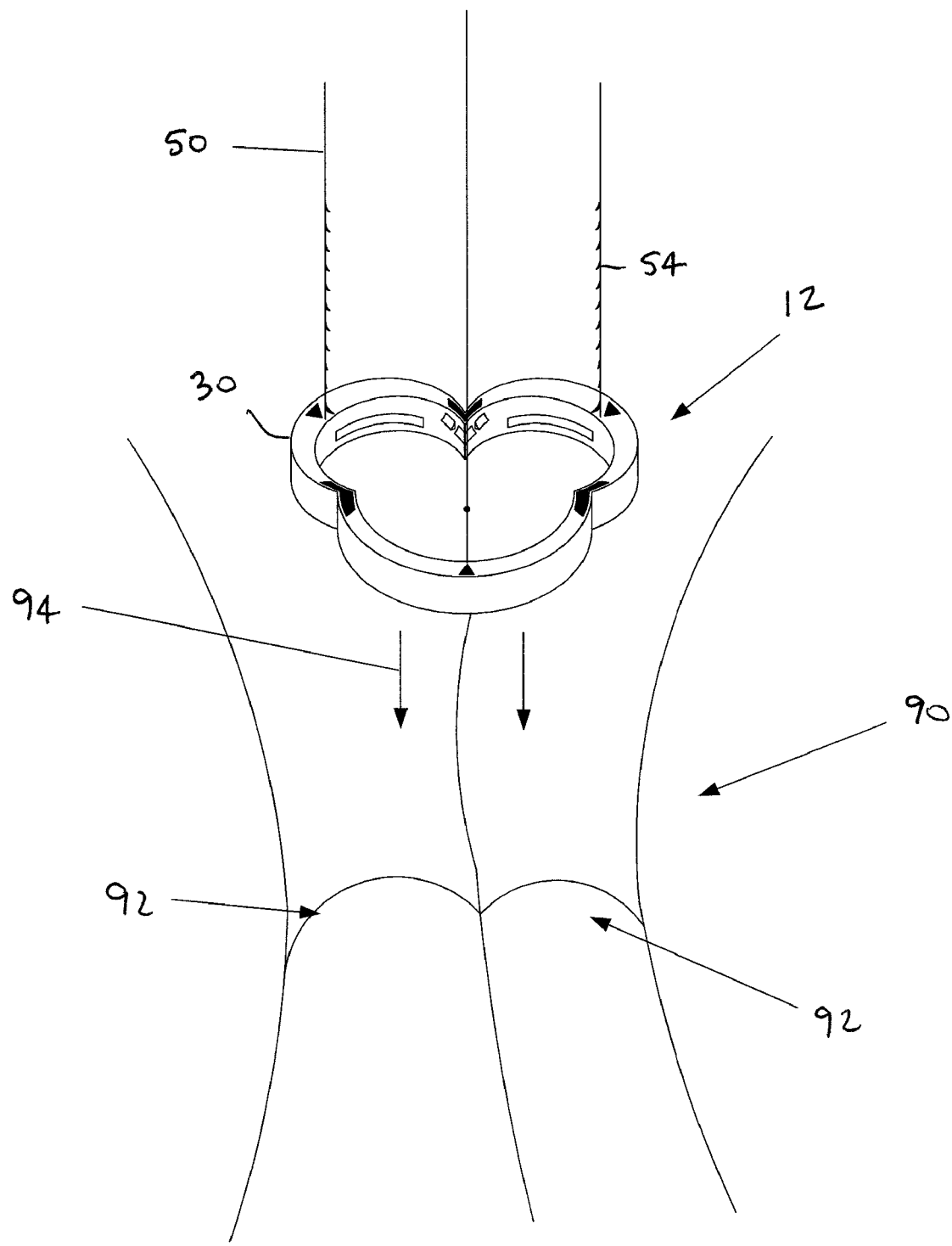
FIGS. 31-35 are cross-sectional views of a biological annulus, showing a method for implanting a heart valve assembly.

As shown in FIG. 31 the base member 12 may be introduced into the annulus 90, as shown by arrows 94. The base member 10 may be carried into the annulus 90 using the holder 60 (not shown) or other tool. If necessary, based upon the anatomy encountered, the shaft 62 of the holder 60 may be bent or otherwise deformed to facilitate accurately placing the base member 12 within the annulus 90. The base member 12 may be oriented before or while being introduced into the annulus 90 such that the lobes 30 of the base member 12 are aligned with the natural lobes 92 of the annulus 90. Once property oriented, the base member 12 be secured within the annulus 90, whereupon the base member 12 may be released from the holder 60, which may then be removed from the annulus 90.

Figure 32:
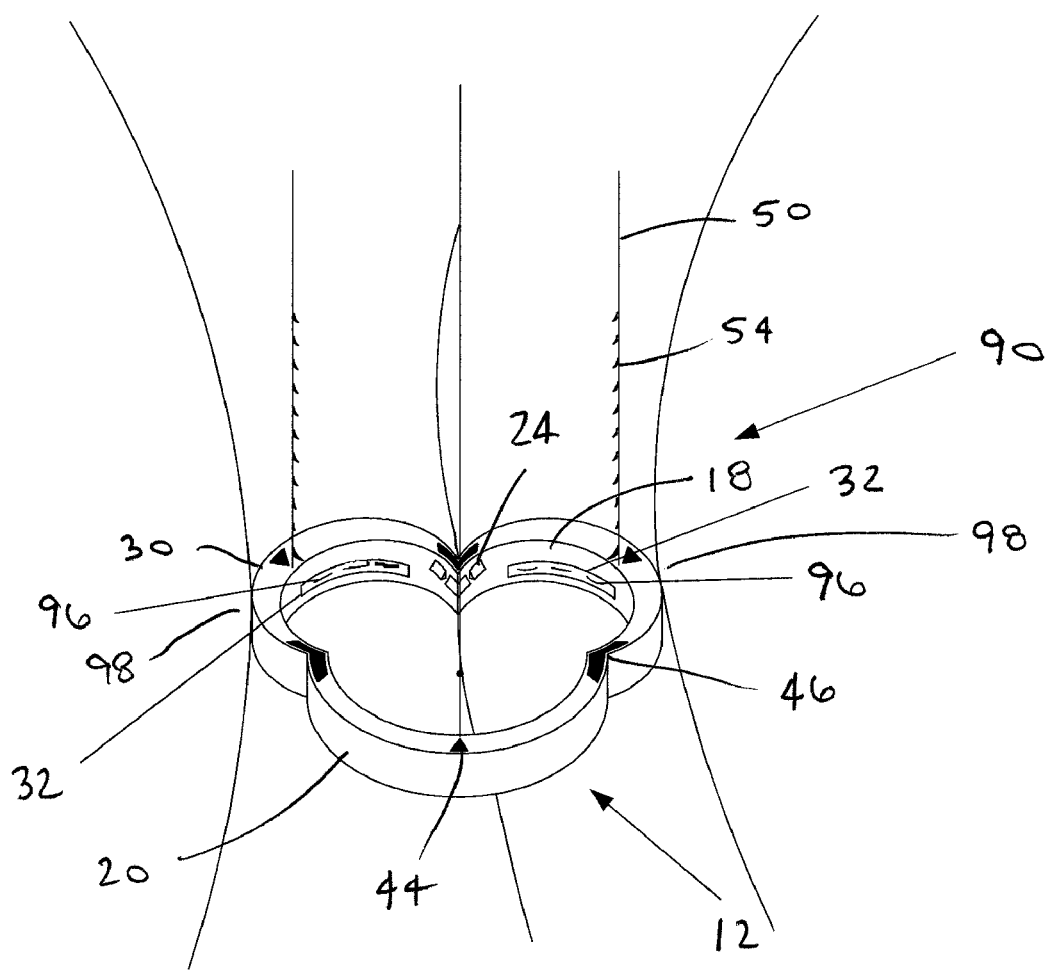

As shown in FIG. 32, the base member 12 is implanted directly within the annulus 90 apart from the crown or valve member 14 (FIG. 1) in an initial implantation state of the heart valve assembly 10. For example, one or more fasteners 96, e.g., clips or sutures (not shown), may be directed through the bas attachment windows 32 into tissue 98 surrounding the annulus 90. For example, a plurality of fasteners (not shown) may be driven through a flexible cuff surrounding an anchoring ring 18 having the windows 32 therein, e.g., spaced apart from one another about the periphery of the base member 12. Exemplary fasteners and methods for using them to implant the base member 12 may be found in U.S. patent application Ser. No. 10/327,821, filed 20 Dec. 2002, Ser. No. 10/646,639, filed 22 Aug. 2003, and Ser. No. 10/681,700 filed 8 Oct. 2003, the entire disclosures of which are incorporated by reference herein.

Alternatively, the base member 12 may be implanted above the biological annulus 90, e.g., within the enlarged space above a natural valve annulus. This configuration may allow a larger heart valve assembly 10 to be implanted, thereby maximizing the open area through which blood may flow through the implantation site. In this configuration, the base member 12 may include a flexible sewing ring (not shown) that may be placed against the tissue above the annulus 90, whereupon one or more fasteners may be driven through the sewing ring into the tissue to secure the base member 12.

As shown in FIGS. 31 and 32, the tethers 50 or other guide members may be attached to the base member 12 when the base member 12 is introduced into the annulus 90. For example, the tethers 50 may be attached to the base member 12 during manufacturing or in preparation for performing the valve implantation procedure. Alternatively, the tethers 50 may be attached to the base member 12 after being deployed in the annulus 90, e.g., by threading the tethers 50 through openings in the base member 12. Preferably, the tethers 50 extend from the outer ends of the lobes 30 of the base member 12, although alternatively, the tethers 50 may extend from the cusps 28 or other locations (not shown).

Turning to FIG. 33, the crown 14 may be introduced into the annulus 90, e.g., using the holder 60. In one embodiment, the leaflets (not shown) may be attached to the crown 14 before the crown 14 is introduced. If the base member 12 includes tethers 50 or other guide members, the tethers 50 may be fed through guide channels (not shown) in the crown 14. If tubular guides (not shown) are provided around the tethers 50, the tubular guides may be fed through the guide channels, which may include their own tubular guides. Once the tethers 50 are inserted through the guide channels, the tubular guides may be removed or may remain to facilitate manipulation of the tethers 50.

The tethers 50 may facilitate aligning the crown 14 with the base member 12, e.g., radially about longitudinal axis 17. The ratcheting elements 54 on the tethers 50 may provide audible and/or tactile feedback to the user as the crown 14 is advanced down the tethers 50 towards the base member 12. In addition or alternatively, visual markers on the crown 14 and/or base member 12, e.g., markers 42, 44 may be monitored directly or via imaging (e.g., x-ray, magnetic resonance imaging (MRI), ultrasound, computed tomography (CT), echocardiogram, and the like), providing feedback regarding the proximity and orientation of the crown 14 relative to the base member 12. In addition or alternatively, the protrusion guide markers 46 may provide tactile feedback of the proximity and orientation of the crown 14.

Figure 34:
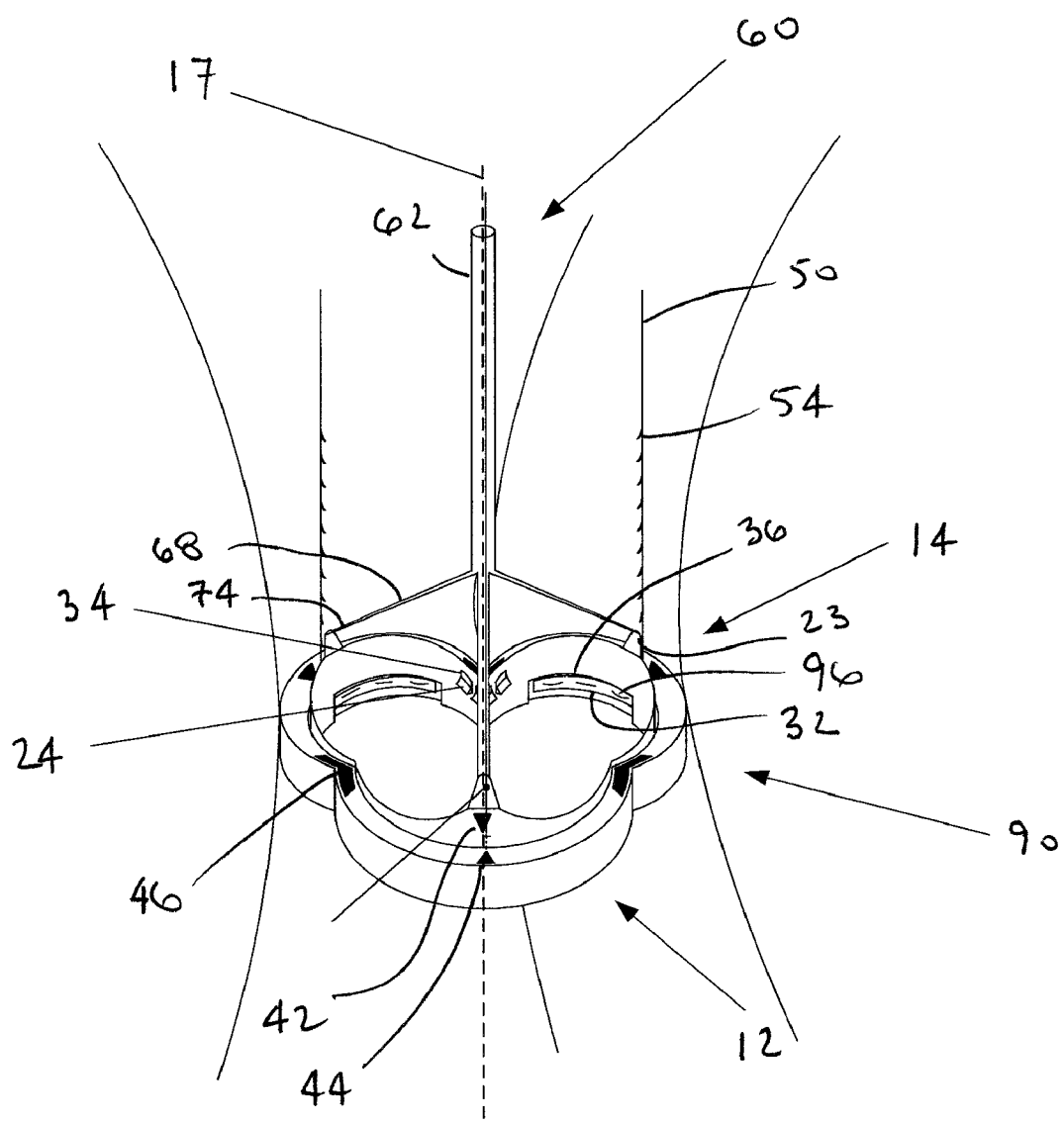

As shown in FIG. 34, once the crown or valve member 14 is oriented and guided into its proper orientation relative to the base member 12, the crown 14 may be deployed and attached to the implanted base member 12 in a final implantation state of the heart valve assembly 10. As shown, as the crown 14 is placed adjacent the base member 12, the crown 14 may at least partially enter the base member 12. Alternatively, the crown 14 may at least partially surround the base member 12 or merely abut the base member 12 (not shown). As the crown 14 is seated against the base member 12, cooperating connectors 34, 24 on the crown 14 and base member 12 may engage one another to substantially secure the crown 14 to the base member 12. For example, as described above, protrusions 24 on the base member 12 may engage within apertures 34 in the crown 14. The connectors 34, 24 may removably or substantially permanently attach the crown 14 to the base member 12. As the protrusions 24 enter into the apertures 34, they may provide audible and/or tactile feedback to the user regarding the proper placement and attachment of the crown 14 and the base member 12.

In addition or alternatively, the tethers 50 may include ratcheting elements (not shown) that engage when the crown 14 is seated against the base member 12. For example, these ratcheting elements may interlock with the guide channels of the crown 14, thereby preventing the crown 14 from being removed from the base member 12. The tethers 50 may then be cut or otherwise disconnected above the crown 14, thereby providing connectors securing the crown 14 to the base member 12. Optionally, the tethers 50 may be knotted to further secure the crown 14 and/or may be welded or fused, e.g., using radio frequency (RF) energy, an adhesive, and the like. Alternatively, if the tethers 50 are removable from the base member 12, the tethers 50 may be removed after the cooperating connectors 42, 44 engage, e.g., by releasing one end of a looped thread defining each tether, and pulling the thread completely out of the base member 12 and crown 14.

Figure 35:
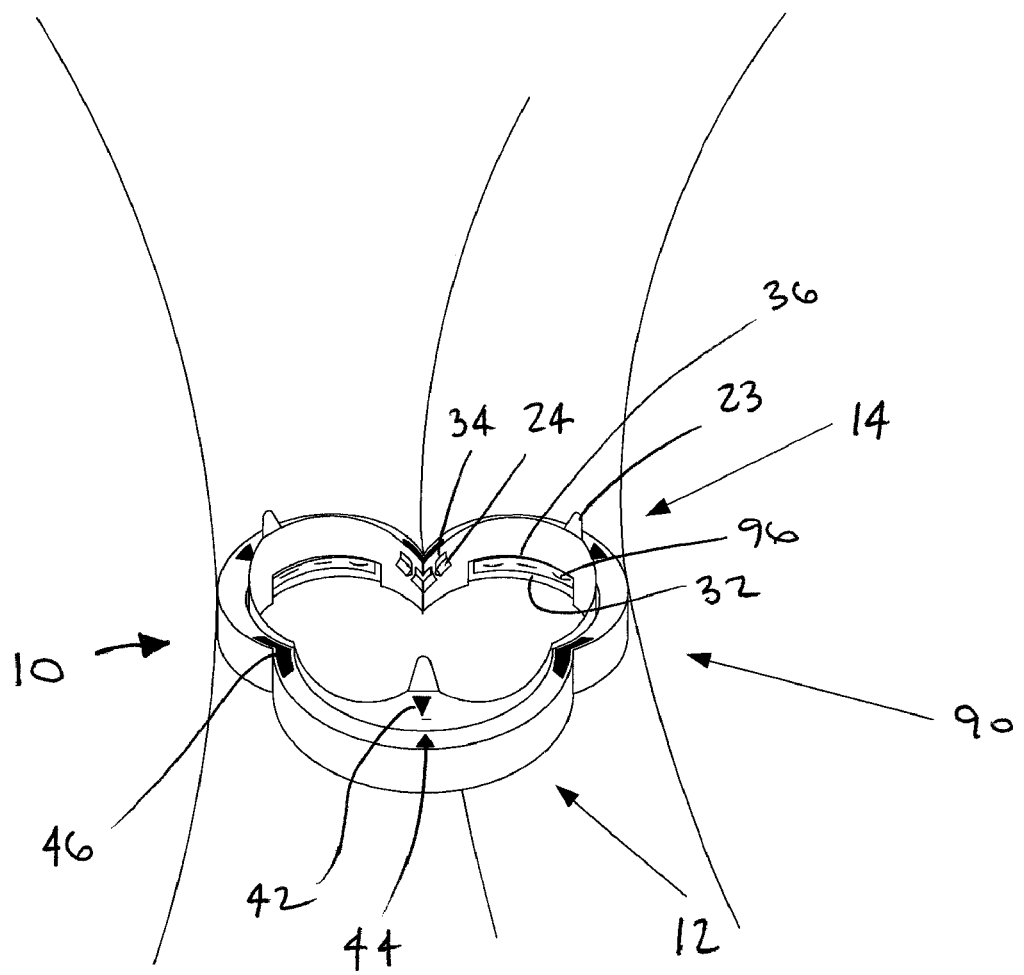

One the crown or valve member 14 is secured to the base member 12, the crown 14 may be released from the holder 60, e.g., by releasing connectors 74, expanding arms 68, and the like, and the holder 60 may be removed. FIG. 35 illustrates the heart valve assembly 10 in the final implantation state once the crown 14 and base member 12 are properly deployed in the annulus 90.

Alternatively, if the crown 14 does not already include leaflets, leaflets (not shown) may be attached to the crown 14 and/or the base member 12, for example, as taught by Lane in U.S. Pat. No. 6,371,983, incorporated by reference above. In a further alternative, if the crown 14 is an intermediate connector, a separate valve member (not shown) may be introduced into the annulus 90 and attached to the crown and/or base member, similar to the embodiments described above. For example, the crown, the base member, and/or the valve member may include guides and/or cooperating connectors for orienting the valve member and/or attaching it to the crown and/or base member, as will be appreciated by those skilled in the art.

Optionally, if it is desirable to remove all or part of the heart valve assembly 10, the crown 14 may be detached and/or removed (not shown) from the base member 12. For example, a tool (not shown) may be introduced into the annulus 90 to depress the protrusions 24 or disengage them (or any other cooperating connectors, not shown) from the apertures 34 to release the crown 14. The crown 14 may then be retrieved, e.g., using the holder 60 or other tool and withdrawn from the annulus 90. Thus, the crown 14 and/or its leaflets or valve body may be replaced, as needed. Optionally, the base member 12 may also be removed by removing the fasteners securing the base member 12 to the annulus 90, as will be appreciated by those skilled in the art.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A heart valve assembly, comprising:
a base member comprising an annular anchor defining a longitudinal axis and a tether attached to and extending away from the annular anchor in a direction of the longitudinal axis and having a ratcheting element; and
a valve member separate from the base member and comprising a guide channel and an annular frame carrying a leaflet, the leaflet attached to the annular frame, wherein the tether is receivable through the guide channel to align the base member with the valve member,
wherein the assembly is configured to provide an initial implantation state in which the base member is implanted into a patient apart from the valve member to provide an implanted base member, the initial implantation state including the annular anchor disconnected from the annular frame, the leaflet attached to the annular frame, the leaflet disconnected from the annular anchor, and the leaflet disconnected from the tether,
and further wherein the assembly is configured to provide a final implantation state in which the valve member is deployed and attached to the implanted base member, the final implantation state including the ratcheting element engaged with the guide channel to prevent the valve member from being directed away from the base member.

2. The assembly of claim 1, further comprising a flexible cuff extending around a periphery of the annular anchor.

3. The assembly of claim 2, wherein the flexible cuff extends radially outwardly from the annular anchor.

4. The assembly of claim 1, further comprising one or more guide markers on at least one of the base member and the valve member for aligning the valve member with the base member about the longitudinal axis before the tether is introduced through the guide channel.

5. The assembly of claim 1, further comprising visual markers on at least one of the base member and the valve member.

6. The assembly of claim 1, wherein the tether is detachable from the base member.

7. The assembly of claim 1, wherein the guide channel comprises a tubular section.

8. The assembly of claim 1, wherein the ratcheting element engages the guide channel to allow the valve member to be directed towards the base member but preventing the valve member from being directed away from the base member.

9. The assembly of claim 1, wherein the ratcheting element secures the valve member adjacent the base member.

10. The assembly of claim 1, wherein the guide channel comprises a cooperating connector for engaging the ratcheting element to allow the valve member to be directed towards the base member but preventing the valve member from being directed away from the base member.

11. The assembly of claim 1, wherein the annular anchor is separate from the annular frame.

12. The assembly of claim 1, wherein the annular anchor is a generally annular shaped body lying in a plane, thereby defining a longitudinal axis orthogonal to the plane, and further wherein the anchor has a noncircular shape within the plane.

\* \* \* \* \*